(12) United States Patent
Sampas et al.

(10) Patent No.: US 10,550,425 B2
(45) Date of Patent: Feb. 4, 2020

(54) COMPOSITION AND METHOD FOR IMPROVING SIGNAL-TO-NOISE IN HYBRIDIZATION TO OLIGONUCLEOTIDE ARRAYS

(71) Applicant: AGILENT TECHNOLOGIES, INC., Santa Clara, CA (US)

(72) Inventors: Nicholas M. Sampas, San Jose, CA (US); Nazumi Alice Yama-Dang, San Jose, CA (US); Paige Anderson, Mountain View, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 21 days.

(21) Appl. No.: 15/351,312

(22) Filed: Nov. 14, 2016

(65) Prior Publication Data
US 2018/0135115 A1 May 17, 2018

(51) Int. Cl.
C12Q 1/68 (2018.01)
C12Q 1/6832 (2018.01)

(52) U.S. Cl.
CPC .................................. C12Q 1/6832 (2013.01)

(58) Field of Classification Search
None
See application file for complete search history.

(56) References Cited

U.S. PATENT DOCUMENTS

| 7,846,660 | B1 | 12/2010 | Albert et al. |
| 7,892,732 | B2 | 2/2011 | Green et al. |
| 8,232,055 | B2 | 7/2012 | Bruhn et al. |
| 2008/0058218 | A1 | 3/2008 | Gordon et al. |
| 2010/0041569 | A1 | 2/2010 | Gentalen et al. |
| 2010/0113296 | A1* | 5/2010 | Myerson ............... C12Q 1/6813 506/9 |
| 2011/0172111 | A1 | 7/2011 | Cantor et al. |
| 2012/0220497 | A1 | 8/2012 | Jacobson et al. |
| 2013/0244884 | A1 | 9/2013 | Jacobson et al. |
| 2013/0296192 | A1 | 11/2013 | Jacobson et al. |
| 2014/0038832 | A1 | 2/2014 | Chee et al. |
| 2015/0148239 | A1* | 5/2015 | Peter ..................... C12Q 1/6841 506/3 |
| 2015/0361422 | A1 | 12/2015 | Sampson et al. |
| 2015/0361423 | A1 | 12/2015 | Sampson et al. |

FOREIGN PATENT DOCUMENTS

| WO | 9746704 A1 | 12/1997 |
| WO | WO2012154201 | * 11/2012 |

OTHER PUBLICATIONS

Barrett, et al. "Comparative genomic hybridization using oligonucleotide microarrays and total genomic DNA", PNAS, 2004, 101(51): 17765-17770.
Kidd, et al. "Mapping and sequencing of structural variation from eight human genomes", Nature, 2008, 453(7197): 56-64.
Yamada, et al. "Visualizaion of Fine-Scale Genomic Structure by Oligonucleotide-Based High-Resolution FISH", Cytogenet. Genome Res., 2011, 132:248-254.
International Search Report and Written Opinion dated Feb. 19, 2018, Application No. PCT/US2017/061530, 18 pages.

* cited by examiner

Primary Examiner — Tracy Vivlemore
Assistant Examiner — Sahana S Kaup

(57) ABSTRACT

Provided herein, among other things, are compositions for improving signal-to-noise in hybridization to oligonucleotide arrays. In some embodiments, the composition may comprise a population of indexing oligonucleotides of formula X-Y, where the sequences of region X hybridize to an array and the sequences of region Y hybridize to distinct sites within a genomic region, transcript, set of transcripts, or complement of the same. Use of these oligonucleotides increases signal, reduces background and smoothens array hybridization analyses. Methods and kits that employ the compositions are also provided.

19 Claims, 5 Drawing Sheets

COMPOSITION AND METHOD FOR IMPROVING SIGNAL-TO-NOISE IN HYBRIDIZATION TO OLIGONUCLEOTIDE ARRAYS

BACKGROUND

Copy number variations can be performed by hybridizing a labeled sample to an oligonucleotide array (see, e.g., Barrett et al. PNAS 2004 51:17765-70, Kidd et al. Nature 2008 453:56-64, U.S. Pat. No. 8,232,055) or by Fluorescent in situ Hybridization (FISH; e.g. Yamada et al, Cytogenet. Genome Res. 2011 132:248-54). However, such methods can sometimes prove challenging, particularly for low abundance samples. Low abundance samples can be amplified, e.g., using whole genome amplification (WGA) methods, prior to analysis. However, it is known that some sequences amplify more efficiently than others and, as such, use of such amplification methods can result in a bias towards some sequences, which increases signal noise. A solution to this problem is described herein.

SUMMARY

This disclosure provides, among other things, a composition for improving signal-to-noise in hybridization to oligonucleotide arrays. In some embodiments, the composition may comprise a population of indexing oligonucleotides of formula X-Y, where the sequences of region X hybridize to an array and the sequences of region Y hybridize to distinct sites within a genomic region, transcript, set of transcripts, or complement of the same. Use of these oligonucleotides is believed to increase signal, reduce background and smoothen data obtained from array hybridization analyses. Methods and kits that employ the compositions are also provided.

Other compositions, systems, methods, features and advantages of the invention will be or will become apparent to one with skill in the art upon examination of the following figures and detailed description. It is intended that all such additional systems, methods, features and advantages be included within this description and be within the scope of the invention.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
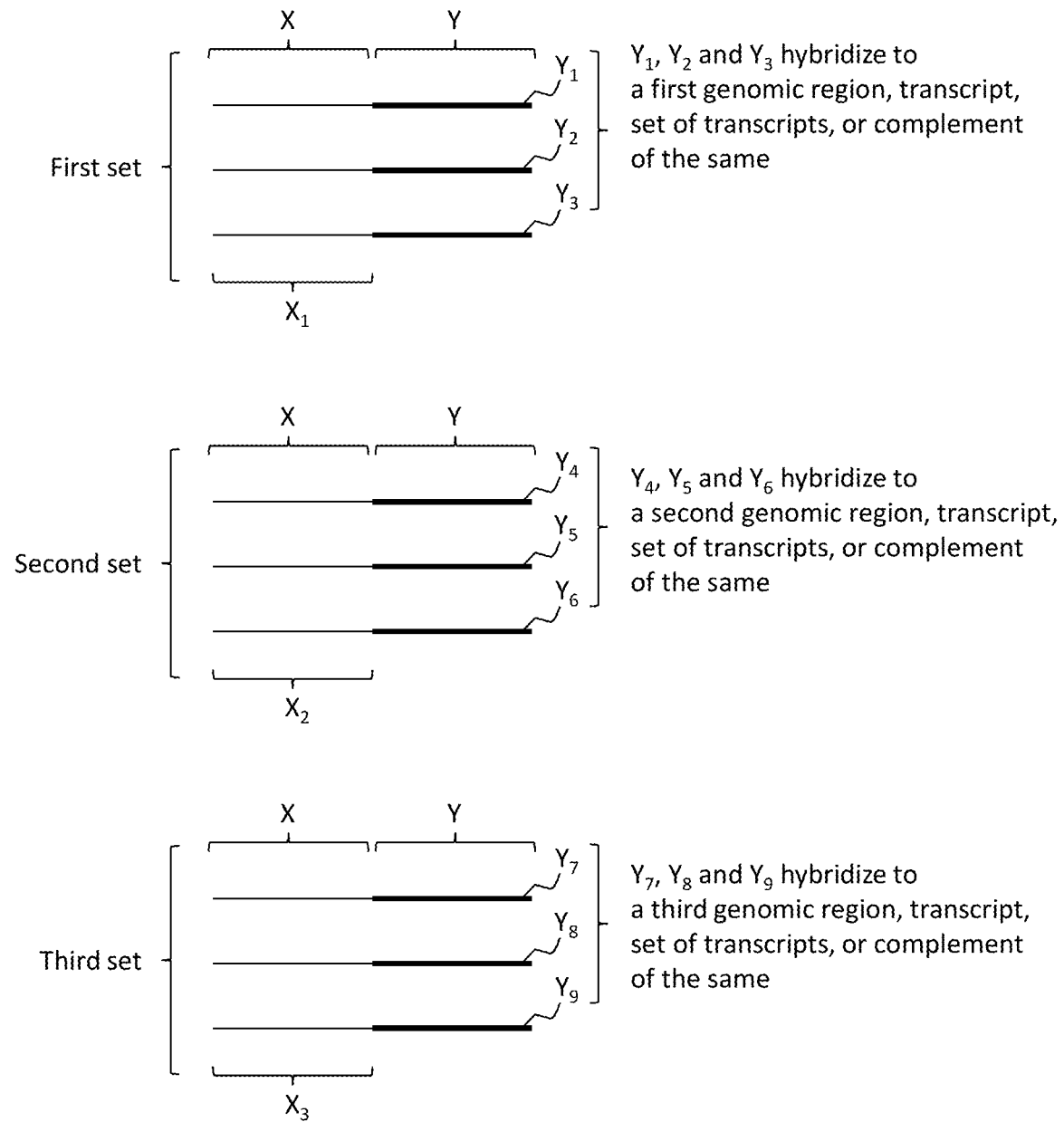
FIG. 1 schematically illustrates a plurality of sets of indexing oligonucleotides of formula X-Y.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "array" is intended to describe a two-dimensional or three-dimensional arrangement of addressable regions bearing oligonucleotides associated with that region. An "array" may be a bead array, in which case the oligonucleotides are attached to beads and the beads may be optically addressable. In other embodiments, the array may be a planar array, in which case the oligonucleotides are attached to a planar support and spatially addressable. The oligonucleotides of an array may be covalently attached to substrate at any point along the nucleic acid chain, but are generally attached at one terminus (e.g. the 3' or 5' terminus).

Any given substrate may carry one, two, four or more arrays disposed on a front surface of the substrate. Depending upon the use, any or all of the arrays may be the same or different from one another and each may contain multiple spots or features. An array may contain at least 10, at least 100, at least 1,000, at least 10,000, at least 100,000, or at least $10^6$ or more features, in an area of less than 20 cm$^2$, e.g., in an area of less than 10 cm$^2$, of less than 5 cm$^2$, or of less than 1 cm$^2$. In some embodiments, features may have widths (that is, diameter, for a round spot) in the range from 1 μm to 1.0 cm, although features outside of these dimensions are envisioned. In some embodiments, a feature may have a width in the range of 3.0 μm to 200 μm, e.g., 5.0 μm to 100 μm or 10 μm to 50 μm. Interfeature areas which do not carry any polymeric compound will typically be present. It will be appreciated though, that the interfeature areas, when present, could be of various sizes and configurations.

Each array may cover an area of less than 100 cm$^2$, e.g., less than 50 cm$^2$, less than 10 cm$^2$ or less than 1 cm$^2$. In some embodiments, the substrate carrying the one or more arrays will be shaped generally as a rectangular or square solid (although other shapes are possible), having a length of more than 4 mm and less than 10 cm, e.g., more than 5 mm and less than 5 cm, and a width of more than 4 mm and less than 10 cm, e.g., more than 5 mm and less than 5 cm.

Arrays can be fabricated using drop deposition from pulse jets of either polynucleotide precursor units (such as monomers) in the case of in situ fabrication, or the previously obtained polynucleotide. Such methods are described in detail in, for example, U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature", "spot" or "area" of the array) is at a particular predetermined location (i.e., an "address") on the array. Array features are typically, but need not be, separated by intervening spaces. As noted above, in some embodiments, an array may be in the form of beads, where each bead corresponds to a feature.

The term "nucleotide" is intended to include those moieties that contain not only the known purine and pyrimidine bases, but also other heterocyclic bases that have been modified. Such modifications include methylated purines or pyrimidines, acylated purines or pyrimidines, or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "nucleic acid" and "polynucleotide" are used interchangeably herein to describe a polymer of any length, e.g., greater than about 2 bases, greater than about 10 bases, greater than about 100 bases, greater than about 500 bases, greater than about 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a multimer of nucleotides from about 2 to 200 nucleotides, up to 500 nucleotides in length. Oligonucleotides may be synthetic or may be made enzymatically, and, in some embodiments, are 30 to 200 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51-60, 61 to 70, 71 to 80, 80 to 100, 100 to 150 or 150 to 200 nucleotides in length, for example. Oligonucleotides can be double stranded or single stranded. Any oligonucleotide can be made from DNA or RNA. An oligonucleotide can be a double-stranded PCR product, a denatured PCR product, a product made by degrading one strand of a double-stranded PCR product, or the product of an in vitro transcription reaction, for example.

An array of polymeric compounds can be made using any suitable method, including methods in which pre-made polymeric compounds are deposited onto the surface of a substrate and then linked to the substrate, and also in situ synthesis methods.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, the term "mixture" is intended to refer to a solution in which the components are interspersed with one another and not spatially separated.

As used herein, the term "aqueous" is intended to refer to a medium in which the solvent comprises water.

As used herein, the terms "sets", "multiple" and "plurality" refer to a population that contains at least 2 members. In certain cases, a plurality may have at least 10, at least 100, at least 1,000, at least 10,000, at least 100,000, at least 106, at least 107, at least 108 or at least 109 or more members.

As used herein, the term "in the solution phase" is intended to refer to a polymeric compound that is in an aqueous environment that is not bound or tethered to a solid substrate. Such a polymeric compound may be dissolved in the aqueous environment.

As used herein, a "mixture of oligonucleotides" refers to an aqueous solution that contains a plurality of different oligonucleotides dissolved therein. A mixture may comprise at least 50, at least 100, at least 500 at least 1,000, at least 5,000, at least 10,000 or at least 50,000 or more of oligonucleotides. A mixture of oligonucleotides may be made by synthesizing the oligonucleotides in situ, i.e., synthesizing the oligonucleotides in place in an array and then cleaving the oligonucleotides from the surface of the array after they have been synthesized. Examples of such methods are described in, e.g., Cleary et al. (Nature Methods 2004 1: 241-248) and LeProust et al. (Nucleic Acids Research 2010

38: 2522-2540). In this example, the oligonucleotides may be cleaved using base (e.g., ammonia or trimethylamine), acid, fluoride or photons, for example.

As used herein, the term "multiple sets", in the context of a composition comprising multiple sets of oligonucleotides, refers to multiple distinct populations of oligonucleotides, where a set of oligonucleotides may comprise at least 2, at least 5, at least 10, at least 50, or at least 100 or more (e.g., 3 to 50, e.g., 4 to 30) oligonucleotides and the composition may contain at least 5, at least 10, at least 50, at least 100, at least 500, at least 1,000 or at least 5,000 or more sets of oligonucleotides.

As used herein, the term "terminal indexer sequence" refers to a unique sequence that occurs at or near the end of a population of oligonucleotides, wherein, the oligonucleotides within each set of oligonucleotides have the same indexer sequence and each set of oligonucleotides has a different indexer sequence. In the present composition region X is a terminal indexer sequence. Indexer sequences are different from one another or their complements. For example, a first unique sequence has a different nucleotide sequence than a second unique sequence or its complement. Indexer sequences do not hybridize to each other, i.e., they have been designed so that they do not anneal to one another under stringent conditions. Examples of such sequences, called "sequence tokens" in certain publications, are described in, e.g., US20070259357 and Brenner et al. (Proc. Natl. Acad. Sci. 1992 89:5381-3), which are incorporated by reference herein. A terminal indexer sequence may be 8-50 bases in length, e.g., 10-35 bases in length. In some instances, a terminal indexer sequence may be up to 100 bases in length.

As used herein, the term "spatially-separating" in the context of spatially-separating different sets of oligonucleotides from one another, refers to separating different sets of oligonucleotides from one another such that the different sets of oligonucleotides are present at different locations on an array (e.g., different beads or different features on a planar support). Specifically, the oligonucleotides in a first set become associated with a first location on an array, the oligonucleotides in a second set become associated with a second location on the array, and the oligonucleotides in a third set become associated with a third location on the array, and so on.

Certain polynucleotides described herein may be referred to by a formula (e.g., "X-Y"). Unless otherwise indicated the polynucleotides defined by a formula may be oriented in the 5' to 3' direction or the 3' to 5' direction. For example, polynucleotides defined by the formula "X-Y" may be "5'-X-Y-3'" or "3'-X-Y-5". The components of the formula, e.g., "X" and "Y", etc., refer to separately definable sequences of nucleotides. In many cases the components of the formula are immediately adjacent to one another in the single molecule. Following convention, the complement of a sequence shown in a formula will be indicated with a prime (') such that the complement of sequence "X" will be "X'". Moreover, unless otherwise indicated or implicit from the context, a polynucleotide defined by a formula may have additional sequence, a spacer, a primer binding site or a molecular barcode, at its 3' end, its 5' end, both the 3' and 5' ends or between regions (e.g., between regions X and Y). As would be apparent, the various component sequences of a polynucleotide (e.g., X and Y, etc.) may independently be of any desired length as long as they capable of performing the desired function (e.g., hybridizing to another sequence). For example, the various component sequences of a polynucleotide may independently have a length in the range of 8-80 nucleotides, e.g., 10-50 nucleotides or 12-30 nucleotides.

The term "variable", in the context of two or more nucleic acid sequences that are variable, refers to two or more nucleic acids that have different sequences of nucleotides relative to one another. In other words, if the polynucleotides of a population have a variable sequence or a particular sequence "varies", then the nucleotide sequence of the polynucleotide molecules of the population varies from molecule to molecule. The term "variable" is not to be read to require that every molecule in a population has a different sequence relative to the other molecules in a population.

If two nucleic acids (e.g., sequences X and X') are "complementary", they hybridize with one another under high stringency conditions. In many cases, two sequences that are complementary have at least 10, e.g., at least 12, at least 15, at least 20 or at least 25 nucleotides of complementarity and in certain cases may have one, two or three non-complementary bases.

The term "does not cross-hybridize" refers to a sequence that does not hybridize to another sequence under stringent hybridization conditions.

The term "genomic region, transcript, set of transcripts, or complement of the same" refers to a contiguous sequence of a genome (e.g., a sequence that is in the range of 1 kb to 100 Mb in length), a contiguous RNA, or a group of RNAs (which RNAs may be co-regulated or functionally related to one another), as well as complements of the RNA or RNAs (i.e., cDNAs made from the same). An RNA can be any type of cellular RNA transcribed by a cell, e.g., an mRNA, a lncRNA, or a small RNA, for example.

The term "sites to which the sequences of region Y hybridize" are sequences in the sample that are complementary to the sequences of region Y.

The term "separated from one another" in the context of sites in a genomic locus, transcript, set of transcripts, or complement of the same, means that the sites are separated from one another by one or more intervening nucleotides (e.g., 1 to 10,000 nucleotides or more).

The term "$T_m$-matched" refers to sequences that have melting temperatures that are within a defined range, e.g., less than 15° C., less than 10° C. or less than 5° C. of a defined temperature.

The term "indexing array" refers to an array, as defined above, containing features that have oligonucleotides that are complementary to the sequences of region X (the terminal indexer sequence) of the present oligonucleotides. An indexing array will have at least one feature that is complementary to the first sequence of region X (e.g., $X_1$), at least one feature that is complementary to the second sequence of region X (e.g., $X_2$), at least one feature that is complementary to the third sequence of region X (e.g., $X_3$), etc.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Indexing Oligonucleotides

FIG. 1 schematically illustrates a plurality of sets of indexing oligonucleotides of formula X-Y. As illustrated, the plurality of sets of indexing oligonucleotides can comprise three sets (a first set, a second set and a third set) of indexing oligonucleotides. However, in practice, there may be at least 2, at least 5, at least 10, at least 50, at least 100, at least 500, at least 1,000, at least 5,000 or at least 10,000 sets of indexing oligonucleotides. As illustrated, each set of indexing oligonucleotides can comprise three indexing oligonucleotides. However, in practice, each set may independently comprises at least 2, at least 5, at least 10, at least 20 or at least 50 indexing oligonucleotides, e.g., 2 to 200 indexing oligonucleotides, 5 to 150 indexing oligonucleotides, or 10 to 100 indexing oligonucleotides.

In some embodiments, the indexing oligonucleotides may have the following general characteristics:

(i) within each set, the sequence of region X is the same. For example, as shown, all of the indexing oligonucleotides in the first set comprise sequence $X_1$, all of the indexing oligonucleotides in the second set comprise sequence $X_2$ and all of the indexing oligonucleotides in the third set comprise sequence $X_3$;

(ii) the sequence of region X varies from set to set. For example, as shown, sequence $V_1$ in the first set of indexing oligonucleotides differs from sequence $V_2$ in the second set of indexing oligonucleotides, and sequence $V_3$ of the third set of indexing oligonucleotides differs from $V_1$ and $V_2$;

(iii) the sequences of region X do not cross-hybridize between the different sets, meaning that, as illustrated, sequences $V_1$, $V_2$ and $V_3$ do not hybridize with one another or the complements of $V_1$, $V_2$ and $V_3$ at high stringency;

(iv) within each set, the sequence of region Y varies. For example, as shown, the indexing oligonucleotides of the first set of indexing oligonucleotides have sequences $Y_1$, $Y_2$ and $Y_3$, which differ from one another, the indexing oligonucleotides of the second set of indexing oligonucleotides have sequences $Y_4$, $Y_5$ and $Y_6$, which differ from one another, and the indexing oligonucleotides of the third set of indexing oligonucleotides have sequences $Y_7$, $Y_8$ and $Y_9$, which differ from one another; and (v) within each set, the sequences of region Y hybridize to sites within the same genomic region, transcript, set of transcripts, or complement of the same. As shown, the sequences of region Y in the first set of indexing oligonucleotides (i.e., $Y_1$, $Y_2$ and $Y_3$) hybridize to distinct sites within a first genomic region, transcript, set of transcripts, or complement of the same, the sequences of region Y in the second set of indexing oligonucleotides (i.e., $Y_4$, $Y_5$ and $Y_6$) hybridize to distinct sites within a second genomic region, transcript, set of transcripts, or complement of the same and the sequences of region Y in the third set of indexing oligonucleotides (i.e., $Y_7$, $Y_8$ and $Y_9$) hybridize to distinct sites within a third genomic region, transcript, set of transcripts, or complement of the same. For example, the sequences of region Y in the first set of indexing oligonucleotides may hybridize to distinct sites within a first genomic region, the sequences of region Y in the second set of indexing oligonucleotides may hybridize to distinct sites within a second genomic region and the sequences of region Y in the third set of indexing oligonucleotides may hybridize to distinct sites within a third genomic region, where the genomic regions may be different, non-overlapping parts of a genome that may have a length in the range of 1 kb to the length of an entire chromosome.

In some embodiments, X and Y may be joined by a linker. The purpose of the linker is to prevent steric hindrance between the region X with its complement and the region Y with its complementary target sequence. In some embodiments, this linker may be a sequence of nucleotides designed to not hybridize any other DNA on the array or in the target sample. The linker may be any molecule that provides appropriate spacing and flexibility to the oligonucleotide construct to prevent steric hindrance across the two regions X and Y. In one embodiment, the linker can be composed of a string (e.g., six) of Ts although, as would be apparent, many sequences will provide the same function.

In some cases, the sequences of region Y in the first set of indexing oligonucleotides may hybridize to distinct sites within a first interval, the sequences of region Y in the second set of indexing oligonucleotides may hybridize to distinct sites within a second interval and the sequences of region Y in the third set of indexing oligonucleotides may hybridize to distinct sites within a third interval, where the first, second and third intervals do not overlap with one another (e.g., they are different chromosomes or different chromosome arms) and are independently in the range of 1 kb to 250 Mb, 1 kb to 100 Mb, 5 kb to 10 Mb, or 10 kb to 500 1 Mb in length.

In other embodiments, the sequences of region Y in the first set of indexing oligonucleotides may hybridize to distinct sites within a first RNA or complement of the same, the sequences of region Y in the second set of indexing oligonucleotides may hybridize to distinct sites within a second RNA or complement of the same and the sequences of region Y in the third set of indexing oligonucleotides may hybridize to distinct sites within a third RNA or complement of the same, where the RNAs are predicted to be transcribed from different genes. Alternatively, the sequences of region Y in the first set of indexing oligonucleotides may hybridize to distinct sites within a first variant of a first gene, the sequences of region Y in the second set of indexing oligonucleotides may hybridize to distinct sites within a second variant of the first gene and the sequences of region Y in the third set of indexing oligonucleotides may hybridize to distinct sites in a third variant of the first gene.

In another embodiment, the sequences of region Y in the first set of indexing oligonucleotides may hybridize to distinct sites within a first set of RNAs or complements of the same (e.g., at least 2, at least 5 or at least 10 RNAs or complements of the same), the sequences of region Y in the second set of indexing oligonucleotides may hybridize to distinct sites within a second set of RNAs or complements of the same (e.g., at least 2, at least 5 or at least 10 RNAs or complements of the same) and the sequences of region Y in the third set of indexing oligonucleotides may hybridize to distinct sites within a third set of RNAs or complements of the same (e.g., at least 2, at least 5 or at least 10 RNAs or complements of the same), where the sets of RNAs or complements of the same are different.

In some embodiments, within each set of indexing oligonucleotides, the sites to which the sequences of region Y hybridize are separated from one another by one or more nucleotides in the genomic region, transcript, set of transcripts, or complement of the same. In other words, there are "gaps" between the sites to which the sequences of region Y hybridize in each set of indexing oligonucleotides. In some embodiments, the average gap between the sites to which region Y hybridizes may be in the range of 50 bases to 100 kb, e.g., 200 bases to 50 kb, or 500 bases to 20 kb. In these embodiments, within each set of indexing oligonucleotides, the sites to which the sequences of region Y hybridize are distributed across a genomic region, with gaps in between. The sequences of Y may be designed programmatically, e.g., using the methods adapted from US20100279883 and US20110039735, for example. In any of these embodiments, because there are gaps, it should not be possible to assemble a synthon (e.g., a synthon that contains a wild type cDNA or a synthon that encodes a protein product) from the sequences of Y within each set.

If the indexing oligonucleotides are RNA oligonucleotides (i.e., composed of rG, rA, rG and rU). Alternatively, the indexing oligonucleotides can be DNA oligonucleotides (which may be double stranded or single stranded). In some embodiments, the indexing oligonucleotides may contain a non-naturally occurring backbone or non-naturally occurring bases.

In some embodiments, the sequences of X are Tm matched, and/or the sequences of Y are Tm matched in that they may independently have melting temperatures that are within a defined range, e.g., less than 15° C., less than 10° C. or less than 5° C. of a defined temperature (e.g., a temperature in the range of 50° C. to 80° C., 65° C. to 85° C.) such that all of the sequences of X and/or all of the sequence of Y will anneal to their targets under the same hybridization conditions.

The sequences of region X and or Y may independently be, in the range of 12 to 150 nucleotides, e.g., 12 to 50 or 12 to 30 nucleotides in length. For example, in some embodiments, all of the sequences of X are 12-50 bases in length, whereas all of the sequences of Y may be 20-100 bases in length.

The total complexity of the plurality of sets of indexing oligonucleotides may be at least 100, at least $10^3$, at least $10^4$, at least $10^5$ or at least $10^6$. In some embodiments, total complexity of the plurality of sets of indexing oligonucleotides may be below $10^5$, $10^6$, $10^7$ or $10^8$. The oligonucleotides may exist as a mixture. This population of oligonucleotides may be made in a variety of different ways. In some embodiments, the oligonucleotides may be made separately and then combined. In some embodiments, the oligonucleotides are made by synthesizing the oligonucleotides in situ, i.e., synthesizing the oligonucleotides in place in an array and then cleaving the oligonucleotides from the surface of the array after they have been synthesized. Examples of such methods are described in, e.g., Cleary et al. (Nature Methods 2004 1: 241-248) and LeProust et al. (Nucleic Acids Research 2010 38: 2522-2540). In some cases, the oligonucleotides may be made in situ, cleaved from the support, amplified by PCR and then transcribed, to produce a population of RNA oligonucleotides. In some cases, the products from several in situ syntheses can be combined. As noted above, the cleaved oligonucleotides may be amplified by PCR to produce a population of double-stranded oligonucleotides, if needed.

As would be apparent, the sequences to which the sequences of Y hybridize may be from a particular species (e.g., from the genome of a eukaryote such as a mammal (e.g., a human or plant). In these embodiments, the sequences of X should not cross-hybridize to any sequence from the same species. Specifically, if the sequences of Y are complementary to a sequence in a mammalian, e.g., human, genome then the sequence of X should not hybridize to any sequences in that genome.

Methods

Figure 2:
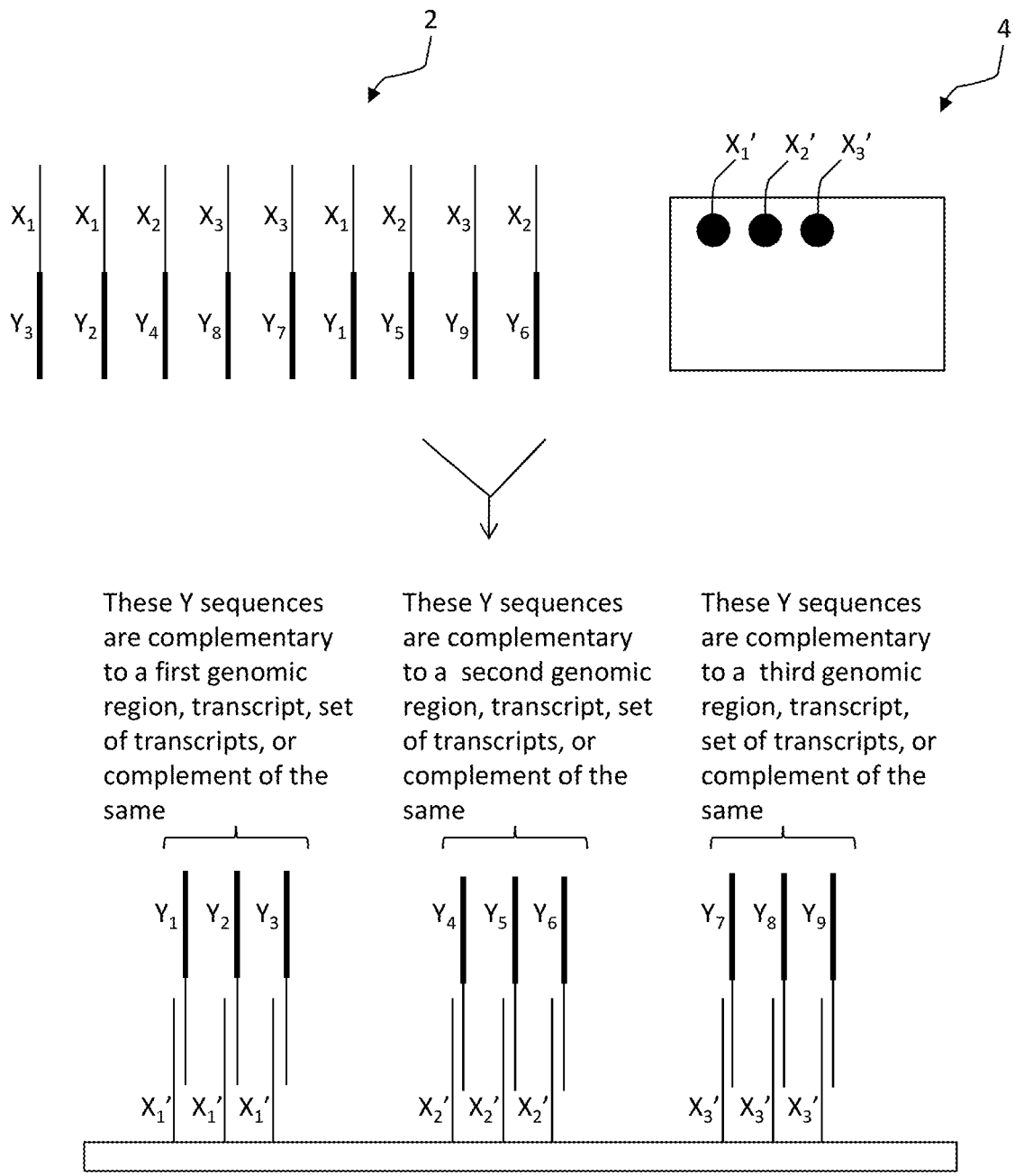
FIG. 2 schematically illustrates how the indexing oligonucleotides hybridize to an indexing array.

With reference to FIG. 2, the indexing oligonucleotides may be used in a method that comprises hybridizing the indexing oligonucleotides 2 with an indexing array 4 that comprises an array of oligonucleotides that are complementary to sequence X, thereby spatially separating the indexing oligonucleotides on the indexing array. Array 4 is an indexing array that comprises an array of oligonucleotides that are complementary to sequence X. In this example, array 4 comprises a single feature having oligonucleotides that comprise sequence $X_1'$ (which is complementary to sequence $X_1$), a single feature having oligonucleotides that comprise sequence $X_2'$ (which is complementary to sequence $X_2$), and a single feature having oligonucleotides that comprise sequence $X_3'$ (which is complementary to sequence $X_3$), as well as other features. In some embodiments, the indexing array may have a least 100 features, e.g., at least 500 features, at least 1,000 features, at least 5,000 features, at least 10,000 features, at least 50,000 features at least 100,000 features or at least 1M features. In some embodiments, each feature on the array comprises an oligonucleotide that is complementary to a sequence of region V in the indexing oligonucleotides. The features of the array may be all different. However, in some embodiments, there may be duplicates for the purpose of redundancy or for noise characterization. The oligonucleotides on the array may be of any length. However, in many embodiments the oligonucleotides on the array are 15 to 75 nucleotides in length. The array may be a bead array or planar array (as illustrated). In some embodiments, the indexing array may comprise a planar substrate and an array of oligonucleotides of formula L-X', wherein: i. within each feature of the array, sequence X' is complementary to a sequence of region X of the indexing oligonucleotides; ii. the sequence of region X' varies from feature to feature; and iii. region L attaches region X' to the substrate. In other embodiments, the indexing array may comprise beads, wherein each bead comprises an oligonucleotide of formula L-X', wherein: i. for each bead, sequence X' is complementary to a sequence of region X of the indexing oligonucleotides; ii. the sequence of region X' varies from bead to bead; and iii. region L attaches region X' to the bead.

The hybridization is typically done under high stringency conditions, which conditions are well known or can be readily derived (see, e.g., Barrett et al, Proc. Natl. Acad. Sci. 2004 101:17765-70 2004). As shown in FIG. 2, after hybridization and an optional wash, the sets of indexing oligonucleotides (which were originally present in a mixture) should spatially separate from one another on the array. In the example shown in FIG. 2, the first set of indexing oligonucleotides hybridizes to the first feature, the second set of indexing oligonucleotides hybridizes to the second feature, and the third set of indexing oligonucleotides hybridizes to the third feature of the array. Some of the principles of how indexing oligonucleotides, or oligonucleotides that comprise terminal indexing sequences, can be spatially separated from one another on an indexing array are described in Sampas (US20150361423).

Figure 3:
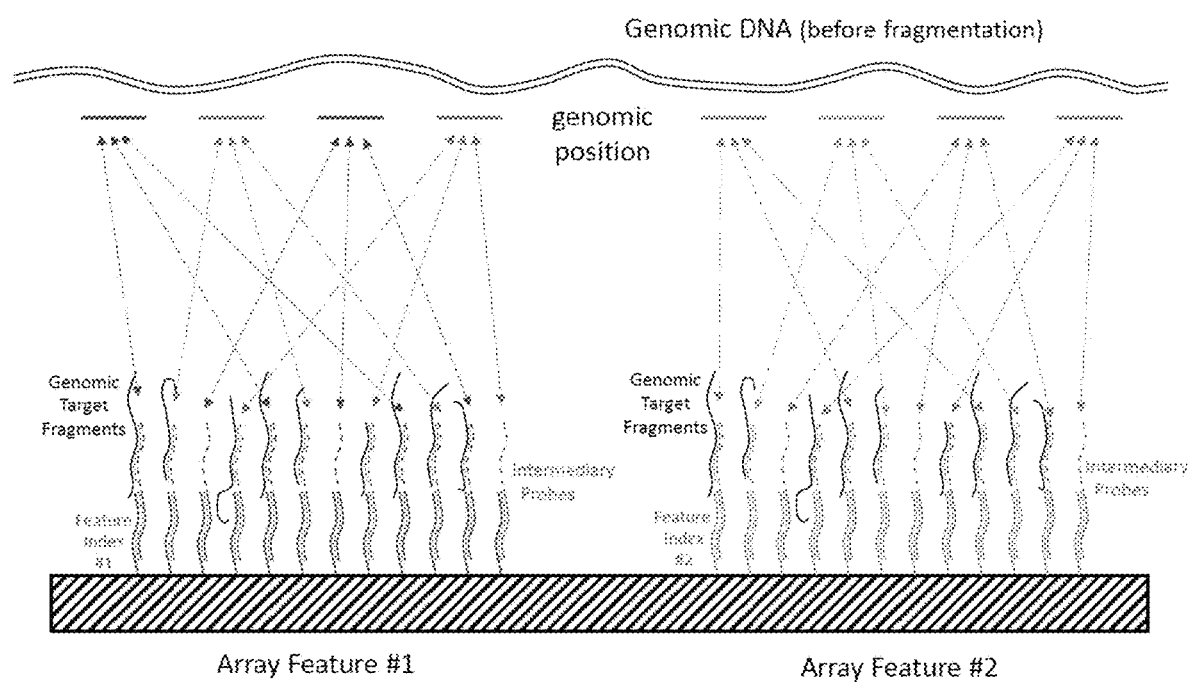
FIG. 3 schematically illustrates how the indexing oligonucleotides are assigned to genomic loci.
Figure 4:
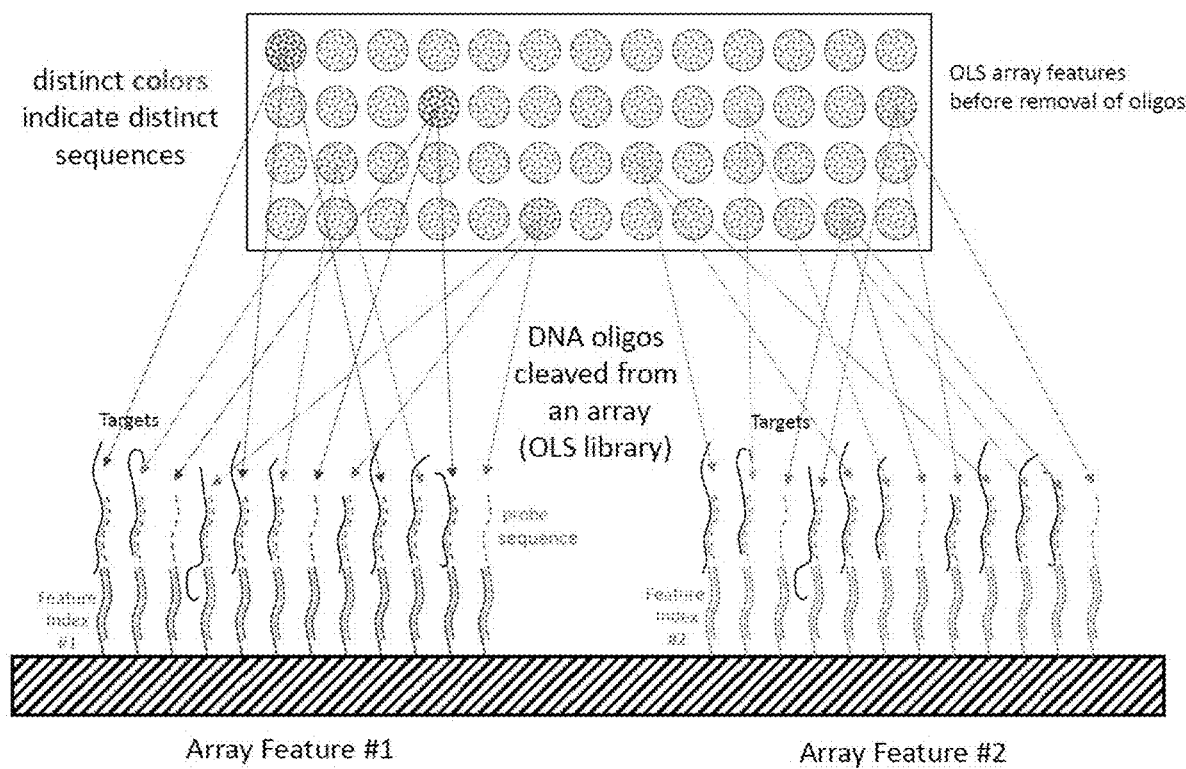
FIG. 4 schematically illustrates how indexing oligonucleotides can be mapped to the features of an indexing array.

In some embodiments, the method involves hybridizing one or more labeled nucleic acid samples (e.g., a labeled sample made from mammalian genomic DNA or RNA) to the indexing oligonucleotide. In these embodiments, the method further comprises: reading (e.g., scanning) the array, thereby determining the abundance of one or more genomic regions, transcripts, set of transcripts, or complement of the same in the one or more samples. This assay may analyze gene expression or a genome. These embodiments are illustrated in FIGS. 3 and 4.

This embodiment may be implemented in a variety of different ways. For example, in some embodiments, the method may be pre-hybridizing the indexing array to the plurality of indexing oligonucleotides and then hybridizing the one or more labeled nucleic acid samples to the indexing oligonucleotides that are hybridized to the array. In other embodiments, the methods may be done by pre-hybridizing the plurality of indexing oligonucleotides to the one or more labeled nucleic acid samples and then hybridizing the indexing oligonucleotides to the indexing array. In other embodiments, the method is done by hybridizing the plurality of indexing oligonucleotides, the one or more labeled nucleic acid samples and the indexing array at the same time.

This method generally results in a composition comprising: a plurality of sets of indexing oligonucleotides, as described above, and an indexing array that comprises an array of oligonucleotides that are complementary to sequence X, where the oligonucleotides are present in a hybridization buffer. In some embodiments, the indexing oligonucleotides are hybridized to the oligonucleotides on the array. In some embodiments, the composition further comprises one or more labeled nucleic acid samples.

A sample may be labeled using methods that are well known in the art (e.g., primer extension, random-priming, nick translation, ULS labeling etc.; see, e.g., Ausubel, et al., Short Protocols in Molecular Biology, 3rd ed., Wiley & Sons 1995, Sambrook et al., Molecular Cloning: A Laboratory Manual, Third Edition, 2001 Cold Spring Harbor, N.Y. and Wiegant et al Cytogenet Cell Genet. 1999 87: 47-52), and, accordingly, such methods do not need to be described here in great detail. In certain embodiments, the test composition is labeled with a fluorescent label, which label will be described in greater detail below.

In certain embodiments, a reference sample may be hybridized, too. In these embodiments, the method comprises hybridizing at least two distinguishably labeled nucleic acid samples to the indexing oligonucleotides, and the method further comprises: reading the array, thereby determining the abundance of one or more genomic regions, transcript, set of transcripts, or complement of the same in the samples. The data obtained from one sample may be compared to the other to provide a comparison. In these embodiments, the samples may be distinguishably labeled using methods that are well known in the art (e.g., primer extension, random-priming, nick translation, end-labeling, etc.; see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.).

The compositions may be labeled using "distinguishable" labels in that the labels can be independently detected and measured, even when the labels are mixed. In other words, the amounts of label present (e.g., the amount of fluorescence) for each of the labels are separately determinable, even when the labels are co-located (e.g., in the same tube or in the same duplex molecule or in the same feature of an array). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), fluorescein and Texas red (Dupont, Boston Mass.), and POPRO3 and TOPRO3 (Molecular Probes, Eugene, Oreg.). Further suitable distinguishable detectable labels may be found in Kricka et al. (Ann Clin Biochem. 39:114-29, 2002).

In some embodiments, the labeling reactions produce first and second populations of labeled nucleic acids that correspond to the sample (i.e. test) and reference nucleic acid compositions, respectively. In some embodiments, the sample(s) may be pre-hybridized with a blocking reagent (e.g., salmon sperm, yeast tRNA, Cot-1 DNA) to suppress repetitive sequences prior to being hybridized to the array, as discussed above, under conditions such that nucleic acid hybridization to the surface bound polynucleotides can occur, e.g., in a buffer containing 50% formamide, 5×SSC and 1% SDS at 42° C., or in a buffer containing 5×SSC and 1% SDS at 65° C., both with a wash of 0.2×SSC and 0.1% SDS at 65° C.

In some embodiments (particularly embodiments in which the sample is limiting), the one or more labeled nucleic acid samples are made by amplifying an initial sample by a whole genome amplification (WGA) method, where the term "whole genome amplification", as used herein, refers to any type of amplification reaction that results in a relatively uniform amplification of substantially all template sequences in a sample (e.g., at least 90% or 95% of the template sequences). Exemplary whole genome amplification methods include degenerate oligonucleotide PCR (DOP-PCR), primer extension preamplification (PEP), and adapter-linker PCR. Whole genome amplification methods include multiple displacement amplification ("MDA"; see Dean et al Proc. Natl. Acad. Sci. 2002 99: 5261-5266 and Nelson Biotechniques 2002 Suppl:44-47), as well as multiple annealing and looping based amplification cycles ("MalBac"; see Zong et al Science. 2012 338:1622-1626), which both involve a limited MDA-based pre-amplification or PicoPLEX, which involves PCR (see, e.g., de Bourcy et al, PLoS One. 2014 9: e105585; Arneson et al Oncol. 2012:710692 and Möhlendick et al, Curr Protoc Cell Biol. 2014 65: 1-22). It is believed that the present approach may reduce any noise or biases that are produced by such methods.

The labeled samples can be contacted to an array(s) serially, or, in other embodiments, simultaneously (i.e., the labeled nucleic acids are mixed prior to their contacting with the array). Depending on how the nucleic acid populations are labeled (e.g., if they are distinguishably or indistinguishably labeled), the populations may be contacted with the same array or different arrays. Where the populations are contacted with different arrays, the different arrays are substantially, if not completely, identical to each other in terms of target feature content and organization in certain embodiments.

Standard hybridization techniques (using high stringency hybridization conditions) are employed in representative embodiments. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For descriptions of techniques suitable for in situ hybridizations see, Gall et al. Meth. Enzymol., 21:470-480 (1981) and Angerer et al. in Genetic Engineering: Principles and Methods Setlow and Hollaender, Eds. Vol 7, pgs 43-65 (plenum Press, New York 1985). See also U.S. Pat. Nos. 6,335,167; 6,197,501; 5,830,645; and 5,665,549; the disclosures of which are herein incorporate by reference. Alternative hybridization conditions are known.

In representative embodiments, comparative hybridization methods comprise the following major steps: (3) hybridization of the nucleic acids to the array, typically under high stringency conditions; (4) post-hybridization washes to remove nucleic acid fragments not bound to the solid support polynucleotides; and (5) detection of the hybridized labeled nucleic acids. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "high stringent hybridization conditions" as used herein refers to conditions that are compatible to produce nucleic acid binding complexes on an array surface between complementary binding members, i.e., between the surface-bound polynucleotides and complementary labeled nucleic acids in a sample. Representative high stringency assay conditions that may be employed in these embodiments are provided above.

The above hybridization step may include agitation of the immobilized polynucleotides and the sample of labeled nucleic acids, where the agitation may be accomplished using any convenient protocol, e.g., shaking, rotating, spinning, and the like.

Following hybridization, the array-surface bound polynucleotides are typically washed to remove unbound labeled nucleic acids. Washing may be performed using any convenient washing protocol, where the washing conditions are typically stringent, as described above.

Following hybridization and washing, as described above, the hybridization of the labeled nucleic acids to the targets is then detected using standard techniques so that the surface of immobilized targets, e.g., the array, is read. Reading of the resultant hybridized array may be accomplished by illuminating the array and reading the location and intensity of resulting fluorescence at each feature of the array to detect any binding complexes on the surface of the array. For example, a scanner may be used for this purpose. Other suitable devices and methods are described in U.S. patent applications: Ser. No. 09/846,125 "Reading Multi-Featured Arrays" by Dorsel et al.; and U.S. Pat. No. 6,406,849, which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of nucleic acids, and are suitable for some embodiments.

Results from the reading or evaluating may be raw results (such as fluorescence intensity readings for each feature in one or more color channels) or may be processed results (such as those obtained by subtracting a background measurement, or by rejecting a reading for a feature which is below a predetermined threshold, normalizing the results, and/or forming conclusions based on the pattern read from the array (such as whether or not a particular target sequence may have been present in the sample, or whether or not a pattern indicates a particular condition of an organism from which the sample came).

In certain embodiments, results are assessed by determining a level of binding of the labeled sample to a feature specific for that genomic region. The term "level of binding" means any assessment of binding (e.g. a quantitative or qualitative, relative or absolute assessment) usually done, as is known in the art, by detecting signal (i.e., pixel brightness) from the label associated with the labeled nucleic acids. Since the level of binding of a labeled test target nucleic acid to a subject split-probe feature is proportional to the level of bound label, the level of binding of labeled sample nucleic acid is usually determined by assessing the amount of label associated with the feature.

In certain embodiments, the methods include evaluating binding of a given feature specific to two populations of target nucleic acids that are distinguishably labeled (i.e., a test and reference sample). In these embodiments, for a single subject split-probe oligonucleotide feature, the results obtained from hybridization with a test and reference sample can be compared, usually after normalization of the data. The results may be expressed using any convenient means, e.g., as a number or numerical ratio, etc. For example, the genomic copy number of a genomic region of interest in a test sample can be evaluated by comparing the level of binding to a specific split-probe of the test sample to a reference sample with a known genomic copy number.

By "normalization" is meant that data corresponding to the two target compositions are globally normalized to each other, and/or normalized to data obtained from controls (e.g., internal controls produce data that are predicted to be equal in value in all of the data groups). Normalization generally involves multiplying each numerical value for one data group by a value that allows the direct comparison of those amounts to amounts in a second data group. Several normalization strategies have been described (Quackenbush et al., Nat Genet. 32 Suppl: 496-501, 2002, Bilban et al., Curr Issues Mol Biol. 4:57-64, 2002, Finkelstein et al., Plant Mol Biol. 48 (1-2):119-31, 2002, and Hegde et al, Biotechniques. 29:548-554, 2000). Specific examples of normalization suitable for use in the subject methods include linear normalization methods, non-linear normalization methods, e.g., using lowest local regression to paired data as a function of signal intensity, signal-dependent non-linear normalization, q-spline normalization and spatial normalization, as described in Workman et al., (Genome Biol. 2002 3, 1-16). In certain embodiments, the numerical value associated with a feature signal is converted into a log number, either before or after normalization occurs. Data may be normalized to data obtained from a support-bound polynucleotide for a genomic region of known copy number and/or methylation status in the target compositions.

In many embodiments, the assessment of the subject methods provides a numerical assessment of binding, and that numeral may correspond to an absolute level of binding, a relative level of binding, or a qualitative (e.g., presence or absence) or a quantitative level of binding. Accordingly, a binding assessment may be expressed as a ratio, whole number, or any fraction thereof.

Further details of the indexing oligonucleotides, indexing arrays and methods for using the same may be found below.

In some embodiments, this approach may increase the signal from each array feature while reducing bias and noise. In some implementations, the approach should also significantly improve the sensitivity of comparative genome hybridization (CGH) assays by reducing the minimal requisite amount of input DNA for the hybridization reaction. In some embodiments, the method works by bringing together numerous distinct labeled target sequences or DNA fragments to each individual array feature by means of intermediary indexing oligonucleotides, where each set of indexing oligonucleotides contains a common indexer sequence that hybridizes to an individual feature. This method is believed to reduce the signal biases and noise observed with a conventional array by capturing a set of labeled fragments by targeting a much longer genomic region with each individual feature. The indexing oligonucleotides to be captured by an array are contained with one or more of OLS (Oligo Library Synthesis) libraries (see LeProust et al. (Nucleic Acids Research 2010 38: 2522-2540). Each OLS library can be constructed with numerous sets of oligonucleotides, and each set of oligonucleotides contains both sequences targeted toward a genomic region and also contains another sequence complementary to a unique indexing sequence of a feature on a DNA array. Alternatively, the indexing oligonucleotides can be generated by high-throughput conventional synthesis of discrete oligonucleotides in tubes or multi-well plates.

This method effectively increases each feature's effective complexity and also increases the signal consistency for application to array CGH. The method can also be applied to other array assays, including gene expression. When using amplified samples, some of the signal noise is a consequence of randomly varying DNA amplification and systematic enzyme biases towards amplifying different genomic regions. These different amplified DNA quantities result in assay noise when the DNA is labeled with a flourophor and detected on a microarray. Some probes are designed to regions that amplify more efficiently and others to regions that do not amplify as well often resulting in inconsistent probe signals for targets that may be the same prior to amplification. This problem is addressed by using indexing oligonucleotides as a means of expanding the targeted sequence coverage and complexity of each feature.

For example, in one embodiment, the array is an indexing array, containing many indexing sequences that do not hybridize to one another or their complements, and which do not hybridize to sequences in the sample (e.g., do not hybridize to the human genome, if the sample is human), where each feature contains a sequence which is different from the others. In another embodiment, the array contains both conventional CGH features designed toward distinct genomic regions as well as indexing features.

Each intermediary oligonucleotide of the OLS library is synthesized such that one portion of each oligo is complementary to an array feature and another portion is complementary to a genomic sequence. Each indexing array feature has numerous corresponding OLS library oligonucleotides, typically all targeting sequences within a contiguous genomic region. The net effect of this construction is that when the assay is performed there is an averaging (or smoothing out) of the varying signals within each region for one index probe, and thus an averaging of amplification biases of the spanned genomic interval for all the target molecules captured by that feature. Another consequence of the use of numerous intermediary molecules capturing multiple target DNA fragments to a single feature is an overall increase in the signal for a given amount of labeled DNA, at least in the case where capture oligo molecules substantially outnumber the targeted gDNA molecules. This increased signal improves the sensitivity of the assay over a conventional assay, where the signals are limited by the number of target molecules targeted by each feature. Another potential consequence is a reduction of the amount of genomic amplification necessary for the assay, and hence potentially a further reduction in bias and noise. And, applications without amplification can benefit by increased sensitivity.

In some embodiments, the span of the targeted genomic interval for each feature is equivalent in the spacing between genomically adjacent CGH probes for a conventional array. For example, Agilent's 60K GenetiSure array has an average spacing of 58 kb between genomic targets. In this example, the effective resolution of each indexing probe is equivalent to the gap between adjacent targeted sequences in a conventional CGH array. After hybridization of the indexing array to the indexing oligonucleotides, each feature will now contain multiple OLS oligonucleotides that can each hybridize to different fragment sequences in the analyte (patient) DNA. Therefore, each feature that conventionally only hybridized to a single analyte molecule can now hybridize to a highly complex set of target sequences from the analyte (patient) DNA and capture a larger number of DNA sequences spanning a given region, resulting in a larger signal than previously possible using a single feature/single sequence system and thus reducing the noise and bias observed from the very small region complementary to a single probe. Indexing features (i.e., the features that are on the array that have sequences that are complementary to the indexing oligonucleotides) can have tens, hundreds, thousands, or more target molecules or sites for each indexing feature.

This method effectively increases the target complexity and potentially increases the fluorophores per feature and, as such, could be applied to single cell or low-input applications. While other approaches have focused on generating more DNA from the analyte, this method solves the problem by improving the feature signal consistency by "casting a wider net" of capture sequences/probes per feature. This new method does not require new enzymes or reagents, additional steps in the lab to be performed, and the workflow is similar to the current workflow, with the small addition of indexed oligonucleotides that may be packaged in the hybridization buffer, pre-hybridized to the arrays or supplied as a separate component that an be added to the sample or the hybridization mixture.

In some embodiments, the indexing oligonucleotides are constructed as DNA libraries. In other embodiments, the intermediary sequences can be RNA nucleotides or RNA libraries. RNA libraries may have several potential advantages: (A) RNA can be constructed by in vitro transcription from DNA to form single-stranded intermediate oligonucleotides. In order to generate a large amount of DNA from an OLS library one can amplify the oligonucleotides resulting in dsDNA. Generating ssDNA from dsDNA is possible by digesting one strand, which adds somewhat to the complexity and the production cost of the reagent. (B) RNA/DNA duplexes are slightly more thermodynamically stable than DNA/DNA duplexes.

In other alternative embodiments non-natural nucleotides or backbones can be used as indexing oligonucleotides. These modifications include nucleotide analogues and non-natural backbone structures, including peptide nucleic acids, locked nucleic acids, etc.

Further, the indexing nucleotides may also have fluorescent residues that act in cooperation with labels on the targeted molecules. For example, one could make a FRET system where the intermediary nucleotides have donor fluorescent molecules and the DNA or RNA target molecules may be labelled with another acceptor fluorophor (or vice versa) such that when hybridization occurs a FRET signal can be detected from the hybridized construct.

There are at least two procedures for implementing the present method. In a first assay, the indexing oligonucleotides are hybridized to the indexing array prior to exposure to the labelled sample(s). In this embodiment, the hybridization may occur at the factory prior to shipping arrays to customers, or by the customer at the bench prior to the sample hybridization. In either case, the concentrations are sufficiently high that the intermediary oligonucleotides are hybridized in the same molarity or in excess relative to the number of indexing feature oligonucleotide molecules, hence saturating the features with intermediaries and providing an equivalent capture oligonucleotide density to that of a conventional CGH array. Reagents, such as salts, PEG, glycerol, agarose, or hydrogels may be used to stabilize the hybridized features before shipping or for long-term storage. In a second assay, both the indexing oligonucleotides and the labeled amplified DNA sample are exposed to the array simultaneously so that the two hybridization events for each indexing oligonucleotide can occur in either order: target-to-intermediary (in solution) before intermediary-to-index (on the surface); or both binding events (intermediary-to-index and intermediary-to-target) on the surface. In this later case, the number of intermediary oligonucleotide molecules for each index should not substantially exceed the number of complementary indexing oligonucleotide molecules on the array. If the library oligonucleotides are in excess, the array signal may or may not be reduced by the competition between target-bound and unbound intermediaries. On the other hand, if the number of intermediaries is lower than the target molecule number, then the signal may or may not be reduced.

In both embodiments, a wash step(s) may be necessary after hybridization to remove unbound and less-specifically bound targets, and maintain the specificity of the assay, just like conventional array CGH.

The assay allows great flexibility in indexing oligonucleotide library design. For example, just like CGH, repetitive, high GC, or other undesirable sequences can be excluded for each targeted region. Or, certain sets of related regions can be targeted for each feature. For example, for a gene expression or a exome-focused CGH assay, all exons of a given gene can be targeted by a single feature, allowing the whole exome to be tiled with a mere 22,000 features, making for a lower cost or smaller array with higher density coverage. Or multiple intermediates can be designed for the same exon. The possibilities for creative oligonucleotides design for different biological purposes are far more substantial than a conventional array.

Kits

Also provided by the subject invention are kits for practicing the subject methods, as described above. The subject kits at least include a plurality of sets of indexing oligonucleotides, as described above and an indexing array, as described above. In some embodiments, the indexing oligonucleotides may be already hybridized to the array. In other embodiments, the indexing oligonucleotides and indexing array may be in separate containers. Other optional components of the kit include: reagents for amplifying a sample by whole genome amplification, blocking reagents (e.g., Cot1 DNA, yeast tRNA or salmon sperm DNA, for blocking repetitive gDNA regions as well as unoccupied regions of the substrate surface), labeling reagents (e.g., fluorescent nucleotides, a polymerase, dNTPs), and/or hybridization reagents (hybridization and wash buffers). In some embodiments, the kit may also contain computer-readable media for performing the subject methods, as discussed above. The various components of the kit may be present in separate containers or certain compatible components may be precombined into a single container, as desired.

In addition to the above-mentioned components, the subject kits typically further include instructions for using the components of the kit to practice the subject methods (i.e., using the split-probe oligonucleotide in a method to evaluate the copy number and/or the methylation of a genomic region of interest). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control analyte mixtures, e.g., two or more control compositions for use in testing the kit.

EXAMPLES

This following assay has been tested on normal samples (without copy number aberrations) and on samples with known copy number aberrations. The effect of indexing has been demonstrated on samples prepared with and without whole genome amplification (WGA), phi29 and PicoPlex. Two array designs, partial and full indexing, were tested in which the number of conventional CGH probes and the number of indexing probes were different. For both designs the conventional CGH probes were selected from the GenetiSure array, commercially sold by Agilent, and were in the Agilent 8-pack (60K) format.

The partial index design had 49,033 conventional CGH probes, leaving 9,774 features on the array for indexing probes to target specific regions of the genome by means of indexing intermediary sequences. For this design, two sets of oligo libraries were designed. Each of these two libraries targeted regions of the genome of commercially available cell lines with known copy number variations of substantial length (>1 Mbp). In a first library, we designed 19 intermediary oligonucleotides for each of the GenetiSure CGH probes. 19 genomically consecutive oligonucleotides were taken from a database of approximately 1 million high-performing CGH probes for each original CGH probe in the region of interest (on the same array). As the average density of probes in the 1 million feature database was 19.5 times greater than the density of CGH probes on the test array the average genomic span of target sites for indexing probes is approximately the same as the average genomic spacing of CGH probes. A similar strategy was used to design a library with 75 intermediary oligonucleotides for each CGH probe, but with each indexing feature spanning a commensurately larger region of the genome from the same database of probes.

Experimentally, the increase in index complexity did not have a significant effect on the reduction of the assay signal to noise ratio or increase in signal under conditions tested (data not shown). The second full design had 1,262 conventional CGH probes distributed along the genome and 56,355 indexing probes. For this design, one set of index sequences were designed with 17 intermediary oligonucletotides per probe following the guidelines described above. For both designs, the CGH probes (X portion) are 45 to 60 bp long, and the indexing sequences (Y portion) are all 40 bp and were designed to a melting temperature of 80° C.

Figure 5:
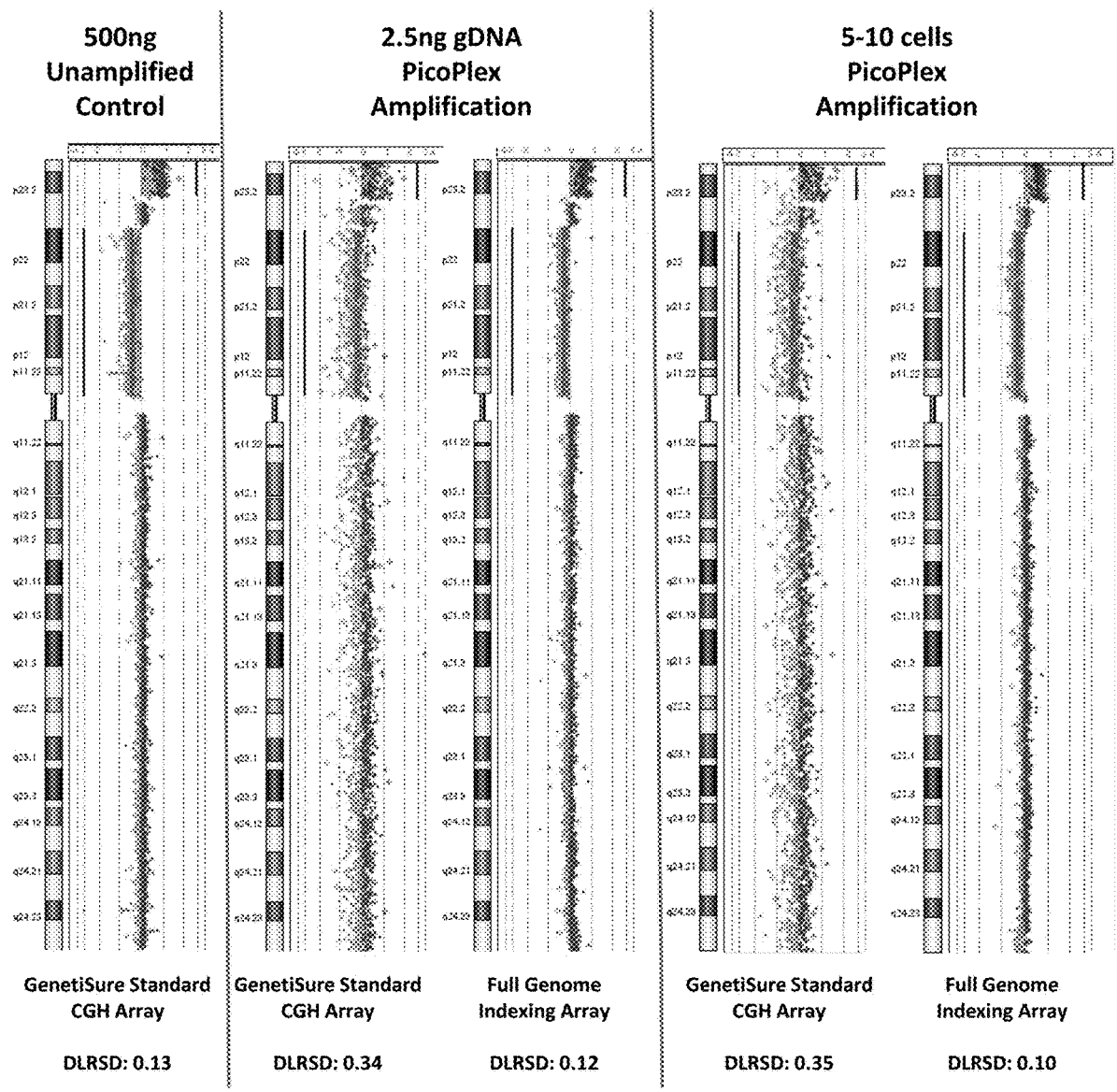
FIG. 5 shows examples of hybridization data.

Examples of hybridization data for the full indexing design is shown in FIG. 5, a number of conditions are compared. What is plotted is the log 2 ratiometric hybridization data between two labeled samples with known aberrant regions for chromosome 8, sample 09552 was labeled in Cy5 and sample 14485 in Cy3 using Agilent's SureTag enzymatic labeling kit. For generation of experimental material, 09552 & 14485 cells, purchased from The Coriell Institute, were grown for gDNA isolations and for collection of discreet cell counts for input into amplification and labeling reactions. For the amplification data shown in FIG. 5, 2.5 ng gDNA or 5-10 cells were amplified (PicoPlex) and fluorescently labeled following Agilent's GenetiSure Pre-Implantation Array-Based CGH for Aneuploidy Screening protocol. For the unamplified control, 500 ng of gDNA was digested with AluI & RsaI restriction enzymes prior to labeling according to the Agilent protocol for Oligonucleotide Array-Based CGH for Genomic DNA Analysis. Cy3 & Cy5 labeled sample pairs were combined and hybridized to either the catalog GenetiSure standard CGH arrays (no indexing) or to the full indexing design arrays following the GenetiSure protocol stated above. For the samples hybridized to the indexing array, indexing oligos (OLS) were added to the hybridization solution in a 1:1.5 molar ratio of probes on the array to indexing oligos respectively. 16 hour hybridizations were performed at 65° C., followed by a stringent wash, fluorescent scanning of the arrays and analysis with Agilent's Genomic Workbench. It can be readily observed by eye that the noise is reduced for the methods that use indexing relative to the standard CGH method. This result is shown quantitatively by the derivative log ratio standard deviation (DLRSD) values reported by the analysis software, a measure of the Cy5/Cy3 signal log ratio noise computed over intervals along the chromosomes. For the unamplified sample 'gold standard' hybridization the DLRSD is 0.13, for the amplified samples with standard CGH the DLRSDs are 0.34 & 0.35, for the 2.5 ng and 5-10 cell inputs respectively. The DLRSD values are 0.1 & 0.12 for the indexing hybs, for the 2.5 ng and 5-10 cell inputs respectively. For WGA (PicoPlex) amplified low input gDNA samples, this indicates a noise reduction of ~3-fold for the indexing arrays over standard array CGH. In all cases the two aberrant regions of ~7 & ~32 Mb of Chromosome 8 were called by the software as being aberrant as can be seen by the black lines in the p-arm of the chromosome.

Similar results were observed when the same samples and input amounts were amplified with phi29 polymerase prior to labeling and hybridization. However, the fold improvement in assay noise reduction with the indexing arrays over standard arrays was on the order of 2-fold.

An initial experiment in which three different index types were compared demonstrated that index oligonucleotides generated by OLS, or RNA constructed by in vitro transcription from the DNA amplified from the OLS or the DNA amplified from the OLS, all reduced the single to noise of the CGH assay with amplified gDNA. However, the different index types do exhibit different characteristics in the assay and would require optimization depending on the indexing method selected.

When the indexes are added to the assay was also explored. Initial experiments were done by pre-hybridizing the OLS oligonucleotide indexes to the array in the absence of the gDNA labeled target, either amplified or not-amplified. The arrays were washed under standard stringent conditions before the hybridization solution with the labeled sample was applied. Subsequent experiments in which the OLS oligonucleotide indexes were added directly to the hybridization solution showed that there was no discernable difference between the two methods on the assay performance in reduction of assay noise, under the conditions chosen. An additional experiment was done in which the labeled target was pre-hybridized to the index OLS oligonucleotides before being added to the index array. Again there was no discernable advantage in the reduction of noise in the assay but differences were seen in the signal levels. Based on this data, it appears that any of the methods so far explored will provide acceptable results.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

EXEMPLARY EMBODIMENTS

Embodiment 1 A plurality of sets of indexing oligonucleotides of formula X-Y, wherein:
  i. within each set, the sequence of region X is the same;
  ii. the sequence of region X varies from set to set;
  iii. the sequences of region X does not cross-hybridize between the different sets;
  iv. within each set, the sequence of region Y varies; and
  v. within each set, the sequences of region Y hybridize to distinct sites within the same genomic region, transcript, set of transcripts, or complement of the same.

Embodiment 2 The plurality of sets of indexing oligonucleotides of embodiment 1, wherein the indexing oligonucleotides are RNA oligonucleotides. Alternatively, the indexing oligonucleotides can be DNA oligonucleotides. If the indexing oligonucleotides are DNA oligonucleotides, then the indexing oligonucleotides may be single-stranded or double-stranded.

Embodiment 3 The plurality of sets of indexing oligonucleotides of any prior embodiment, wherein the plurality of sets of indexing oligonucleotides comprises at least 2, at least 5, at least 10, at least 50, at least 100, at least 500, at least 1,000, at least 5,000 or at least 10,000 sets of indexing oligonucleotides.

Embodiment 4 The plurality of sets of indexing oligonucleotides of any prior embodiment, wherein each set comprises at least 2, at least 5, at least 10, at least 20 or at least 50 indexing oligonucleotides, e.g., 2 to 200 indexing oligonucleotides, 5 to 150 indexing oligonucleotides, or 10 to 100 indexing oligonucleotides.

Embodiment 5 The plurality of sets of indexing oligonucleotides of any prior embodiment, wherein, within each set, the sites to which the sequences of region Y hybridize are separated from one another in the genomic locus, transcript, set of transcripts, or complement of the same. In these embodiments, the average gap between the sites to which region Y hybridizes is in the range of 100 bases to 100 kb, e.g., 200 bases to 50 kb, or 500 bases to 20 kb.

Embodiment 6 The plurality of sets of indexing oligonucleotides of any prior embodiment, wherein, within each set, the sites to which the sequences of region Y hybridize are distributed across a genomic region that is in the range of 1 kb to the length of a chromosome, e.g., e.g., 1 kb to 250 Mb, 1 kb to 100 Mb, 5 kb to 10 Mb, 10 kb to 500 1 Mb in length.

Embodiment 7 The plurality of sets of indexing oligonucleotides of any prior embodiment, wherein, within each set, the sites to which the sequences of region Y hybridize can be within a single mRNA transcript, or set of alternative transcripts of the same gene.

Embodiment 8 The plurality of sets of indexing oligonucleotides of any prior embodiment, wherein the sequences of X are Tm matched.

Embodiment 9 The plurality of sets of indexing oligonucleotides of any prior embodiment, wherein the sequences of Y are Tm matched.

Embodiment 10 The plurality of sets of indexing oligonucleotides of any prior embodiment wherein region X is in the range of 12 to 150, e.g., 12 to 80 or 12 to 60 nucleotides in length.

Embodiment 11 The plurality of sets of indexing oligonucleotides of any prior embodiment, wherein region Y is in the range of 12 to 150, e.g., 20 to 120 or 20 to 80 nucleotides in length.

Embodiment 12 A method comprising hybridizing a plurality of indexing oligonucleotides of any of embodiments 1-11 with an indexing array that comprises an array of oligonucleotides that are complementary to sequence X, thereby spatially separating the indexing oligonucleotides on the indexing array.

Embodiment 13 The method of embodiment 12, wherein the indexing array has a least 100 features, e.g., at least 500 features, at least 1,000 features, at least 5,000 features or at least 10,000 features.

Embodiment 14 The method of any prior method embodiment, wherein the method further comprises hybridizing one or more labeled nucleic acid samples (e.g., a labeled sample made from mammalian genomic DNA or RNA) to the indexing oligonucleotides, and the method further comprises: reading the array, thereby determining the abundance of one or more genomic regions, transcript, set of transcripts, or complement of the same in the one or more samples. In any method embodiment, the method may be employed for gene expression analysis. In other embodiments, the method may be employed for genome analysis (e.g., for comparative genome hybridization).

Embodiment 15 The method of embodiment 14, wherein the method is done by pre-hybridizing the indexing array to the plurality of indexing oligonucleotides and then hybridizing the one or more labeled nucleic acid samples to the indexing oligonucleotides that are hybridized to the array.

Embodiment 16 The method of embodiment 14, wherein the method is done by pre-hybridizing the plurality of indexing oligonucleotides to the one or more labeled nucleic acid samples and then hybridizing the indexing oligonucleotides to the indexing array.

Embodiment 17 The method of embodiment 14, wherein the method is done by hybridizing the plurality of indexing oligonucleotides, the one or more labeled nucleic acid samples and the indexing array at the same time.

Embodiment 18 The method of any of embodiments 12-17, wherein the one or more labeled nucleic acid samples are made by amplifying an initial sample by a whole genome amplification (WGA) method.

Embodiment 19 The method of any of embodiments 12-18, wherein the method comprises hybridizing at least two distinguishably labeled nucleic acid samples to the indexing oligonucleotides, and the method further comprises: reading the array, thereby determining the abundance of one or more genomic regions, transcript, set of transcripts, or complement of the same in the samples. The data obtained from one sample may be compared to the other to provide a comparison.

In any embodiment, the array may be a bead array or planar array.

Embodiment 20 The method of any prior method embodiment, wherein the indexing array may comprise a planar substrate and an array of oligonucleotides of formula L-X', wherein: i. within each feature of the array, sequence X' is complementary to a sequence of region X of the indexing oligonucleotides; ii. the sequence of region X' varies from feature to feature; and iii. region L attaches region X' to the substrate.

Embodiment 21 The method of any prior method embodiment, wherein the indexing array may comprise beads, wherein each bead comprises an oligonucleotide of formula L-X', wherein: i. for each bead, sequence X' is complementary to a sequence of region X of the indexing oligonucleotides; ii. the sequence of region X' varies from bead to bead; and iii. region L attaches region X' to the bead.

Embodiment 22 A kit comprising: a plurality of sets of indexing oligonucleotides of any of embodiments 1-11, and an indexing array that comprises an array of oligonucleotides that are complementary to sequence X.

The array may be a bead array or planar array.

Embodiment 23 The kit of any prior kit embodiment, wherein the indexing array comprises a planar substrate and an array of oligonucleotides of formula L-X', wherein: i. within each feature of the array, sequence X' is complementary to a sequence of region X of the indexing oligonucleotides; ii. the sequence of region X' varies from feature to feature; and iii. region L attaches region X' to the substrate.

Embodiment 24 The kit of any prior kit embodiment, wherein the indexing array comprising beads, wherein each bead comprises an oligonucleotide of formula L-X', wherein: i. for each bead, sequence X' is complementary to a sequence of region X of the indexing oligonucleotides; ii. the sequence of region X' varies from bead to bead; and iii. region L attaches region X' to the bead.

Embodiment 25 The kit of any prior kit embodiment, wherein the indexing oligonucleotides are hybridized to the array.

Embodiment 26 The kit of any prior kit embodiment, wherein the indexing oligonucleotides and indexing array are in separate containers Embodiment 27 The kit of any prior kit embodiment, further comprising reagents for amplifying a sample by whole genome amplification.

Embodiment 28 The kit of any prior kit embodiment, further comprising blocking reagents.

Embodiment 29 The kit of any prior kit embodiment, further comprising labeling reagents.

Embodiment 30 The kit of any prior kit embodiment, further comprising hybridization reagents.

Embodiment 31 A composition comprising: a plurality of sets of indexing oligonucleotides of any of embodiments 1-11; and an indexing array that comprises an array of oligonucleotides that are complementary to sequence X.

Embodiment 30 The composition of embodiment 31, wherein the composition further comprises one or more labeled nucleic acid samples.

Embodiment 31 The composition of embodiment 29 or 30, wherein the oligonucleotides are present in a hybridization buffer.

In any embodiment, the array may be a bead array or planar array.

Embodiment 32 The composition of any prior composition embodiment, wherein the indexing array comprises a planar substrate and an array of oligonucleotides of formula L-X', wherein: i. within each feature of the array, sequence X' is complementary to a sequence of region X of the indexing oligonucleotides; ii. the sequence of region X' varies from feature to feature; and iii. region L attaches region X' to the substrate.

Embodiment 33 The composition of any prior composition embodiment, wherein the indexing array comprises beads, wherein each bead comprises an oligonucleotide of formula L-X', wherein: i. for each bead, sequence X' is complementary to a sequence of region X of the indexing oligonucleotides; ii. the sequence of region X' varies from bead to bead; and iii. region L attaches region X' to the bead.

What is claimed is:

1. A kit comprising:
   a plurality of sets of indexing oligonucleotides of formula X-Y, wherein:
   i. within each set, the sequence of region X is the same;
   ii. the sequence of region X varies from set to set;
   iii. the sequences of region X do not cross-hybridize between the different sets;
   iv. within each set, the sequence of region Y varies; and
   v. within each set, the sequences of region Y hybridize to distinct sites within the same genomic region, transcript, set of transcripts, or complement of the same; and
   an indexing array that comprises an array of oligonucleotides that are complementary to sequence X.

2. The kit of claim 1, wherein the indexing oligonucleotides are hybridized to the indexing array in separate containers.

3. The kit of claim 1, wherein the plurality of sets of indexing oligonucleotides comprises at least 50 sets of indexing oligonucleotides.

4. The kit of claim 1, wherein each set comprises at least 10 indexing oligonucleotides.

5. The kit of claim 1, wherein, within each set, the sites to which the sequences of region Y hybridize are separated from one another within the genomic region, transcript, set of transcripts, or complement of the same.

6. The kit of claim 5, wherein, within each set, the sites to which the sequences of region Y hybridize are separated from one another by gaps of about 100 bp to about 100 kb.

7. The kit of claim 1, wherein, within each set, the sites to which the sequences of region Y hybridize are distributed across a genomic region that is about 1 kb to about one chromosome in length.

8. The kit of claim 1, wherein, within each set, the sites to which the sequences of region Y hybridize are within a single mRNA transcript, or set of alternative transcripts of a given gene.

9. The kit of claim 1, wherein the sequences of X are Tm matched, and the sequences of Y are Tm matched.

10. The kit of claim 1, wherein region X is about 12 nucleotides to about 60 nucleotides in length.

11. The kit of claim 1, wherein region Y is about 20 nucleotides to about 70 nucleotides in length.

12. The kit of claim 1, wherein the indexing oligonucleotides are RNA oligonucleotides.

13. The kit of claim 1, wherein the indexing oligonucleotides are double-stranded or single stranded DNA oligonucleotides.

14. A method comprising hybridizing the plurality of sets of indexing oligonucleotides of the kit of claim 1 with the indexing array, thereby spatially separating the indexing oligonucleotides on the indexing array.

15. The method of claim 14, wherein the indexing array has a least 100 features.

16. The method of claim 14, wherein the method further comprises:
   hybridizing one or more labeled nucleic acid samples to the indexing oligonucleotides, and
   reading the array, thereby determining the abundance of one or more genomic regions, transcript, set of transcripts, or complement of the same in the one or more samples.

17. The method of claim 16, wherein the method is done by:

pre-hybridizing the indexing array to the plurality of indexing oligonucleotides and then hybridizing the one or more labeled nucleic acid samples to the indexing oligonucleotides that are hybridized to the array;

pre-hybridizing the plurality of indexing oligonucleotides to the one or more labeled nucleic acid samples and then hybridizing the indexing oligonucleotides to the indexing array; or hybridizing the plurality of indexing oligonucleotides, the one or more labeled nucleic acid samples and the indexing array at the same time.

18. The method of claim 16, wherein the one or more labeled nucleic acid samples are made by amplifying an initial sample by a whole genome amplification method.

19. The method of claim 16, wherein the method comprises hybridizing at least two distinguishably labeled nucleic acid samples to the indexing oligonucleotides, and the method further comprises:

reading the array, thereby determining the abundance of one or more genomic regions, transcript, set of transcripts, or complement of the same in the samples.

\* \* \* \* \*